(12) United States Patent
Takata

(10) Patent No.: US 11,654,155 B2
(45) Date of Patent: May 23, 2023

(54) THERAPEUTIC MATERIAL FOR SKIN ULCER

(71) Applicants: Hideyasu Takata, Saitama (JP); Omoidesouzou Co., Ltd., Tokyo (JP)

(72) Inventor: Hideyasu Takata, Saitama (JP)

(73) Assignees: Hideyasu Takata, Saitama (JP); OMOIDESOUZOU CO., LTD., Tokyo (JP)

( * ) Notice: Subject to any disclaimer, the term of this patent is extended or adjusted under 35 U.S.C. 154(b) by 0 days.

(21) Appl. No.: 15/518,256

(22) PCT Filed: Jun. 19, 2015

(86) PCT No.: PCT/JP2015/003086
§ 371 (c)(1),
(2) Date: Apr. 11, 2017

(87) PCT Pub. No.: WO2016/059735
PCT Pub. Date: Apr. 21, 2016

(65) Prior Publication Data
US 2017/0304334 A1    Oct. 26, 2017

(30) Foreign Application Priority Data

Oct. 16, 2014   (JP) .............................. JP2014-211768

(51) Int. Cl.
| | | |
|---|---|---|
| *A61K 31/70* | (2006.01) | |
| *A61K 38/00* | (2006.01) | |
| *A61K 31/7036* | (2006.01) | |
| *A61K 45/00* | (2006.01) | |
| *A61L 15/44* | (2006.01) | |
| *A61K 33/06* | (2006.01) | |
| *A61L 26/00* | (2006.01) | |
| *A61K 31/00* | (2006.01) | |
| *A61K 33/00* | (2006.01) | |
| *A61L 15/46* | (2006.01) | |
| *A61L 15/34* | (2006.01) | |
| *A61L 15/18* | (2006.01) | |
| *C07H 19/20* | (2006.01) | |

(52) U.S. Cl.
CPC .......... *A61K 31/70* (2013.01); *A61K 31/7036* (2013.01); *A61K 33/06* (2013.01); *A61K 38/00* (2013.01); *A61K 45/00* (2013.01); *A61L 15/18* (2013.01); *A61L 15/34* (2013.01); *A61L 15/44* (2013.01); *A61L 15/46* (2013.01); *A61L 26/0004* (2013.01); *C07H 19/20* (2013.01); *A61K 31/00* (2013.01); *A61K 33/00* (2013.01); *A61L 26/00* (2013.01); *A61L 2300/406* (2013.01); *A61L 2300/412* (2013.01); *A61L 2300/414* (2013.01)

(58) Field of Classification Search
CPC .... A61K 31/70; A61K 38/00; A61K 31/7036; A61K 45/00; A61K 33/06; A61K 31/00; A61K 33/00; A61L 15/44; A61L 15/46; A61L 15/34; A61L 15/18; A61L 26/0004; A61L 2300/412; A61L 2300/414; A61L 2300/406; A61L 26/00; A61L 15/28; A61L 15/40; C07H 19/20; A61P 9/00; A61P 17/02; A61P 17/00

See application file for complete search history.

(56) References Cited

U.S. PATENT DOCUMENTS

| | | | | |
|---|---|---|---|---|
| 3,767,784 A | * | 10/1973 | Gluck ................... | A61L 15/225 514/774 |
| 4,524,064 A | * | 6/1985 | Nambu ................. | A61L 15/225 424/445 |

(Continued)

FOREIGN PATENT DOCUMENTS

| | | |
|---|---|---|
| EP | 0314109 A2 | 5/1989 |
| EP | 1872788 A1 | 1/2008 |
| JP | 2005-112795 A | 4/2005 |

(Continued)

OTHER PUBLICATIONS

Pierce et al. (American Journal of Pathology vol. 140 1992, 1375-1388).*
Ichioka et al. (Journal of Wound Care vol. 14, No. 3; Mar. 2005; p. 105-109).*
Frank et al. (Can Fam Physician 2005;51:1352-1359).*
Founder et al. (J. Am. Acad. Dermatol. Febuary 2008; vol. 58, iss 2: pp. 185-206).*

(Continued)

*Primary Examiner* — Aradhana Sasan
(74) *Attorney, Agent, or Firm* — Edwin S. Flores; Daniel J. Chalker; Chalker Flores, LLP

(57) ABSTRACT

It is an object to provide a therapeutic material for a skin ulcer which has excellent therapeutic effects on intractable skin ulcers such as decubitus ulcers with pockets and huge decubitus ulcers. By applying the therapeutic material for decubitus ulcers consisting of a fibrous material holding an antibiotic and a cell proliferation accelerator therein which is formed into an approximately spherical shape to a site of decubitus in a state in which a defect extending to the dermis, subcutaneous tissue, muscle or bone occurs, it is possible to treat critical skin ulcers such as intractable decubitus ulcers with pockets and huge intractable decubitus ulcers, as well as to treat not only relatively mild decubitus classified as stage II according to the US National Pressure Ulcer Advisory Panel (NPUAP) staging system, i.e., decubitus having ulcers in a state in which a part of the dermis is deficient, but also severe decubitus that has progressed to stage III to IV according to the NPUAP staging system, particularly decubitus with intractable ulcers with pockets or decubitus with huge intractable ulcers.

11 Claims, 2 Drawing Sheets

(56) References Cited

U.S. PATENT DOCUMENTS 5,827,247 A * 10/1998 Kay .................. C08L 5/04
604/327
2007/0154510 A1 * 7/2007 Wilcher ............ A61F 13/00034
424/422

FOREIGN PATENT DOCUMENTS

| JP | 2008-044916 A | 2/2008 |
|---|---|---|
| JP | 2012-149053 A | 8/2012 |

OTHER PUBLICATIONS

Edsberg, et al., J Wound Ostomy Continence Nurs. 2016;43(6):585-597.*
Saskatoon Health Region Nursing Practice Committee, Wound Irrigation and Packing, Sep. 2013.*
British Columbia Provincial Nursing Skin & Wound Committee, Procedure: Wound Packing, Aug. 2017.*
Hisamitsu et al., "Toin ni Okeru Jokuso Chiryo Keiken", Yamaguchi-Ken Igakkaishi, No. 42, pp. 158-159, Mar. 2008 [Partial English translation].
Ito et al., Reconstruction of the Soft Tissue of a Deep Diabetic Foot Wound with Artificial Dermis and Recombinant Basic Fibroblast Growth Factor, Plastic & Reconstructive Surgery, 115(2), pp. 567-572, Feb. 2005 [Partial English translation].
Nagata et al., "Jokuso Chiryoyaku o Kushi shite Kanchi shieta Nanjisei Kyodai Ryokatai Kaiyo no Ichirei" Japanese Journal of Pressure Ulcer, vol. 10, No. 3, p. 441, P-074, 2008 [Partial English translation].
Yamaguchi et al., "A Case of Pressure Ulcer in a Nursing Home, Cured Using an IT-based Support System of Pharmacists", Journal of Japanese Society of Hospital Pharmacists, vol. 44, No. 1, pp. 136-139, 2008.
Translation of the International Preliminary Report on Patentability [PCT/JP2015/003086] dated Apr. 27, 2017.
Jiang W et al: "Improved wound healing in pressure-induced decubitus ulcer with controlled release of basic fibroblast growth factor", Journal of Alloys and Compounds, Elsevier Sequoia, Lausanne, CH, vol. 159, No. 1-2, Jul. 14, 2008 (Jul. 14, 2008),. pp. 508-514.
Extended European Search Report EP 15850657.6 dated May 30, 2018.

* cited by examiner

[Figure 1]
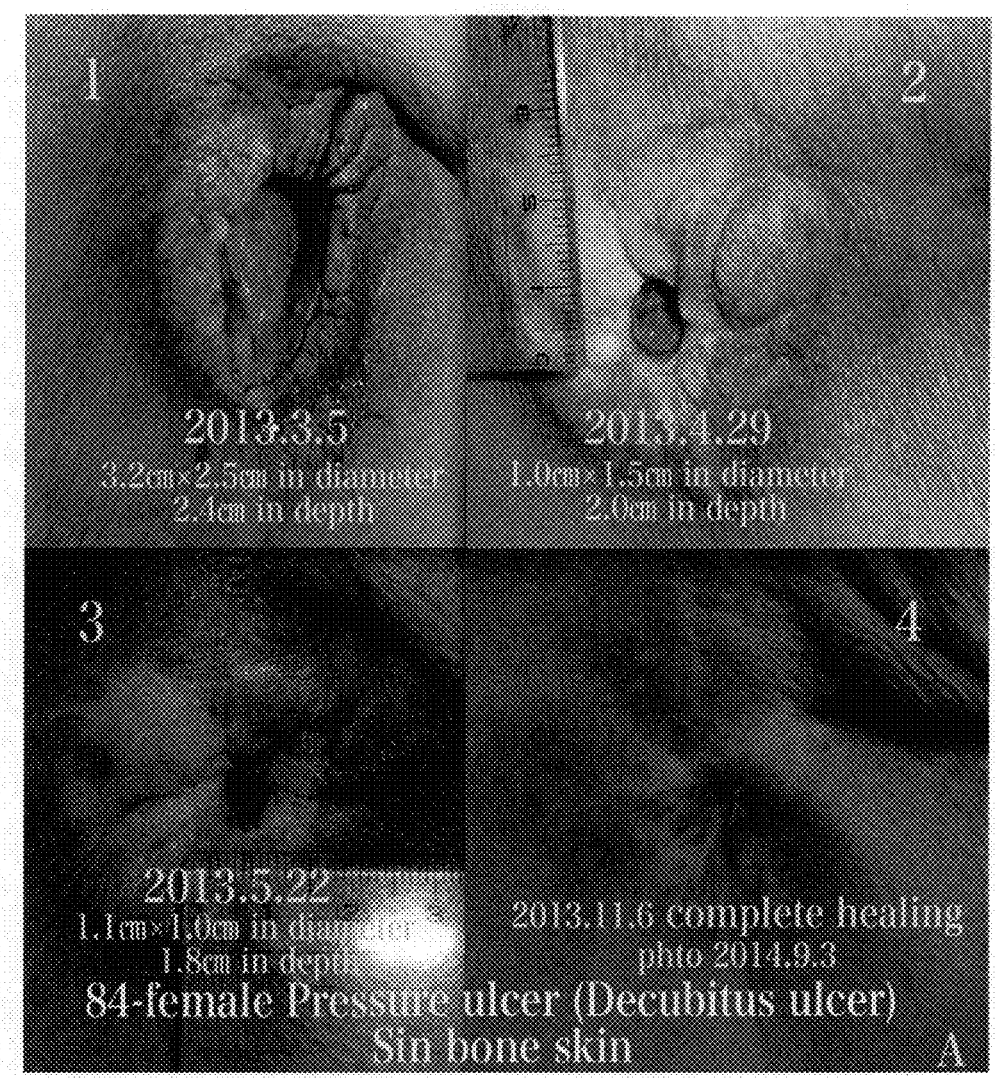

[Figure 2]
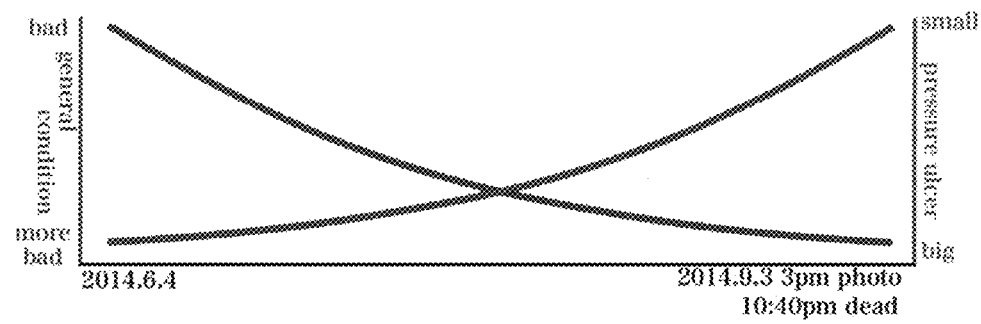
Although the patient died of deterioration of general condition, ulcers were markedly ameliorated in three months.

THERAPEUTIC MATERIAL FOR SKIN ULCER

CROSS-REFERENCE TO RELATED APPLICATIONS

This application is the National Stage of International Application No. PCT/JP2015/003086, filed on Jun. 19, 2015 claiming the priority of JP 2014-211768, filed on Oct. 16, 2014, the content of each of which is incorporated by reference herein.

TECHNICAL FIELD

The present invention relates to a therapeutic material for a skin ulcer, in which forming a fibrous material holding an antibiotic and a cell proliferation accelerator therein as active ingredients into an approximately spherical shape (dumpling shape) enables long-term contact over a large area of the antibiotic and the cell proliferation accelerator with the inner surface of a skin ulcer in a state where a defect extending to the dermis, subcutaneous tissue, muscle or bone due to decubitus and the like occurs.

BACKGROUND ART

Skin ulcers are intractable diseases in which skin tissues are deficient due to decubitus (bed sores), burns, arterial occlusive disease, diabetes, and the like. Particularly, since elderly individuals, patients with arterial occlusive disease, patients with diabetes and the like are reduced in blood circulation, skin ulcers, when occur, may become severe and may require a long period of time for healing. When the skin ulcers are prolonged, they may lead to bacterial infection and thereby to the death of patients. Therefore, it is desirable to heal wounded site in a short period of time.

Decubitus ulcer refers to a pathological condition in which local blood flow is inhibited by compression of the skin and, as a result, skin tissues are damaged by circulatory failure and it is prone to occur in not only bedridden elderly people but also disabled people, people with malnutrition, people with poor resilience and the like.

The mild decubitus in which the damage of skin tissue does not extend beyond the epidermis is relatively easy to heal. However, the severe decubitus in which a skin defect (decubitus ulcer) is formed extending to the dermis, subcutaneous tissue, muscle (ligament) or bone is intractable, and in some cases sepsis occurs concomitantly and may result in death. Particularly when decubitus progresses to stage III to IV according to the US National Pressure Ulcer Advisory Panel (NPUAP) Staging System or when pockets occur concurrently with decubitus, it is often difficult to treat.

Decubitus is prone to occur in such regions as the sacral region, the greater trochanter region and the calcaneus region as well as the occipital node, the ischial tuberosity and the lateral lower leg compartment. Methods for preventing decubitus by postural change or massage have been used, but these methods have taken a lot of effort to perform continuously. However, as patients with decubitus often have a poor general condition, decubitus cannot be sufficiently prevented by such methods.

Materials and methods for treating decubitus have also been developed actively. For example, Patent Document 1 discloses that oral administration of icosapentaenoic acid to patients with decubitus ameliorated decubitus. However, this document describes nothing but that progression of decubitus of approximately stage II according to the IAET (International Association Enterostomal Therapy) Classification was inhibited and has not revealed whether decubitus ulcers and ulcers with pockets can be healed. Patent Document 2 discloses that use of an ointment for treating decubitus containing bamboo extract in combination with an oral formulation for treating decubitus containing marine collagen, isomaltooligosaccharide and ceramide saccharide could heal decubitus ulcers of stage 2 to 3 according to the Ohura classification (ulcers with about 1.7 cm×1.7 cm in size). However, this document has not revealed whether ulcers with pockets can be healed or whether ulcers that have progressed to stage III to IV according to the NPUAP Staging System can be healed. Patent Document 3 disclose that skin ulcer could be healed by applying a gauze having ozonized olive oil containing oleate ozonide adhered and permeated thereto to a patient with skin ulcer. However, this document has not revealed whether decubitus ulcers can be healed or whether ulcers with pockets can be healed. Many other therapeutic methods for decubitus are known such as a systemic therapy (nutritional management, zinc administration and the like), a therapeutic method using a topical formulation (such as an ointment, spray and paste) or a wound dressing (dressing materials), surgical treatment, debridement, decompression therapy, but these therapeutic methods could not sufficiently treat decubitus ulcers with pockets, huge intractable decubitus and critical skin ulcers.

PRIOR ART DOCUMENTS

Patent Documents

Patent Document 1: Japanese unexamined Patent Application Publication No. 2012-149053
Patent Document 2: Japanese unexamined Patent Application Publication No. 2008-44916
Patent Document 3: Japanese unexamined Patent Application Publication No. 2005-112795

SUMMARY OF THE INVENTION

Object to be Solved by the Invention

It is an object of the present invention to provide a therapeutic material for a skin ulcer which has excellent therapeutic effects on intractable skin ulcers such as decubitus ulcers with pockets and huge decubitus ulcers.

Means to Solve the Object

Sofratulle patch (manufactured by Sanofi), which is a patch containing as an active ingredient fradiomycin sulfate having an antibacterial action, is also used in the treatment of mild decubitus in which the damage of skin tissue does not extend beyond the epidermis to treat or prevent bacterial infections arising from a skin damage site. On the other hand, Fiblast Spray 500 (manufactured by Kaken Pharmaceutical Co., Ltd.), which is a spray-type therapeutic agent for skin ulcers containing as an active ingredient trafermin having an angiogenic action and granulation promoting action, is used in the treatment of decubitus to promote repair and regeneration of skin with defects.

While the present inventor has diligently continued treatment in order to solve the problem mentioned above, the inventor has thought that if fradiomycin sulfate (antibiotic) could be effectively adhered and leached out throughout the interior portion of the ulcers with pockets to effectively inhibit bacterial infection in the ulcers, the angiogenesis and granulation promoting actions of trafermin (angiogenesis and granulation promoting agent) in the ulcers could be maximized to treat the intractable decubitus ulcers. Accordingly, the inventor has found that the intractable decubitus can be treated or ameliorated, when several sheets of Sofratulle patch are used not for its intended use as the patch but are formed into a dumpling shape or folded depending on the size of the ulcer with a pocket, sprayed with Fiblast Spray 500 until sufficiently impregnated with a trafermin solution and are packed in the ulcer with a pocket to effectively adhere and leach out fradiomycin sulfate and trafermin throughout the interior portion of the ulcers, and he thus has completed the present invention.

The present invention relates to (1) a therapeutic material for a skin ulcer, consisting of a fibrous material holding an antibiotic and a cell proliferation accelerator therein which is formed into an approximately spherical shape, wherein the therapeutic material is for applying to a site of a skin ulcer in a state in which a defect extending to the dermis, subcutaneous tissue, muscle or bone occurs; (2) the therapeutic material according to (1), wherein the skin ulcer is a decubitus ulcer; (3) the therapeutic material according to (1) or (2), wherein the fibrous material is cotton; (4) the therapeutic material according to any one of (1) to (3), wherein the cell proliferation accelerator has angiogenesis and/or a granulation promoting actions; (5) the therapeutic material according to any one of (1) to (4), wherein the cell proliferation accelerator is trafermin; (6) the therapeutic material according to any one of (1) to (5), wherein the antibiotic is fradiomycin sulfate; or (7) the therapeutic material according to any one of (2) to (6), wherein the decubitus is a decubitus classified as stage III to IV when the degree of progression of the decubitus is classified according to the US National Pressure Ulcer Advisory Panel (NPUAP) staging system.

The present invention also relates to (8) use of a fibrous material holding an antibiotic and a cell proliferation accelerator therein in the manufacture of a therapeutic material for a skin ulcer for applying to a site of a skin ulcer in a state in which a defect extending to the dermis, subcutaneous tissue, muscle or bone occurs; or (9) use according to (8), wherein the skin ulcer is a decubitus ulcer.

As other embodiments of the present invention, mention can be made of a method for treating a skin ulcer comprising applying to a site of a skin ulcer in a state in which a defect extending to the dermis, subcutaneous tissue, muscle or bone occurs, or a fibrous material holding an antibiotic and a cell proliferation accelerator therein which is formed into an approximately spherical shape, for applying to a site of a skin ulcer in a state in which a defect extending to the dermis, subcutaneous tissue, muscle or bone occurs.

Effect of the Invention

As the therapeutic material for a skin ulcer according to the present invention has excellent therapeutic effects on critical skin ulcers such as intractable decubitus ulcers with pockets and huge intractable decubitus, it is effective for the treatment of critical skin ulcers caused by traumas, burns, infections, decubitus, arterial occlusive disease, diabetes, scleroderma, radiation, Behcet's disease and the like. The therapeutic material for a skin ulcer according to the present invention is effective for the treatment of not only relatively mild decubitus classified as stage II according to the NPUAP Staging System, i.e., decubitus having ulcers in a state in which a part of the dermis is deficient, but also severe decubitus that has progressed to stage III to IV according to the NPUAP Staging System, particularly decubitus with intractable ulcers with pockets or decubitus with huge intractable ulcers.

BRIEF DESCRIPTION OF DRAWINGS

FIG. 1 is a figure indicating the course of treatment for an ulcer with a pocket caused by decubitus in case 2.

FIG. 2 The upper section of FIG. 2 is a figure indicating the course of treatment for a huge ulcer caused by decubitus in case 3. The lower section of FIG. 2 is a figure indicating the relationship between the course of treatment ("pressure ulcer" in the Figure) and a general condition ("general condition" in the Figure) for a huge ulcer caused by decubitus in case 3.

MODE OF CARRYING OUT THE INVENTION

The therapeutic material for a skin ulcer according to the present invention (hereinafter referred to simply as "therapeutic material of the present invention") is characterized in that: it consists a fibrous material which holds an antibiotic and a cell proliferation accelerator therein (permeated throughout it and/or adhered to it); and is formed into an approximately spherical shape (a dumpling shape); it is applied to a site of a skin ulcer in a state in which a defect extending to the dermis, subcutaneous tissue, muscle or bone occurs; and the antibiotic and the cell proliferation accelerator are brought into contact with the inner surface of a skin ulcer with (having) an undermining state (pocket) in which a hollow is present under the skin surrounding the skin ulcer or into contact with the inner surface of a huge skin ulcer for long periods of time. Examples of the therapeutic material for a skin ulcer according to the present invention include: an approximately spherical shaped fibrous material holding an antibiotic therein which has a cell proliferation accelerator held therein; an approximately spherical shaped fibrous material holding a cell proliferation accelerator therein which has an antibiotic held therein; an approximately spherical shaped fibrous material which has an antibiotic and a cell proliferation accelerator held therein; as well as an approximately spherical shaped fibrous material adhering an antibiotic which has been formed by forming non-approximately spherical shaped (for example, sheet-shaped) fibrous material adhering an antibiotic into a dumpling shape or by folding it, and which has a cell proliferation accelerator held therein; an approximately spherical shaped fibrous material holding a cell proliferation accelerator therein which has been formed by forming a non-approximately spherical shaped (for example, sheet-shaped) fibrous material holding a cell proliferation accelerator therein into a dumpling shape or by folding it, and which has an antibiotic held therein; an approximately spherical shaped fibrous material which has been formed by forming a non-approximately spherical shaped (for example, sheet-shaped) fibrous material into a dumpling shape or by folding it, and which has an antibiotic and a cell proliferation accelerator held therein; an approximately spherical shaped fibrous material holding an antibiotic and a cell proliferation accelerator therein, formed by forming a non-approximately spherical shaped (for example, sheet-shaped) fibrous material holding an antibiotic therein which has a cell proliferation accelerator held therein into a dumpling shape or by folding it; an approximately spherical shaped fibrous material holding an antibiotic and a cell proliferation accelerator therein, formed by forming a non-approximately spherical shaped (for example, sheet-shaped) fibrous material holding a cell proliferation accelerator therein which has an antibiotic held therein into a dumpling shape or by folding it; and an approximately shaped fibrous material holding an antibiotic and a cell proliferation accelerator therein, formed by forming a non-approximately spherical shaped (for example, sheet-shaped) fibrous material which has an antibiotic and a cell proliferation accelerator held therein into a dumpling shape or by folding it.

If necessary, the therapeutic material of the present invention may be added with or hold such ingredients as conventional pharmaceutically acceptable carriers, binders, stabilizers, excipients, diluents, pH buffers, disintegrators, isotonic agents, additives, coating agents, solubilizers, lubricating agents, gliding agents, solubilizing agents, lubricants, flavoring agents, sweetening agents, solvents, gelling agents and nutrients further added or held therein. Specifically, examples of such an ingredient include water, physiological saline, animal fat and oil, vegetable oil, lactose, starch, gelatin, microcrystalline cellulose, gum, talc, magnesium stearate, hydroxypropylcellulose, polyalkylene glycol, polyvinyl alcohol and glycerin.

As used herein, "skin ulcer" refers to conditions in which at least a part of the dermis is deficient or damaged due to some cause such as traumas, thermal burns, infections, decubitus, arterial occlusive disease, diabetes, scleroderma, radiation or Behcet's disease, preferably due to decubitus. The skin ulcer according to the present invention include conditions caused by the further progression of the skin ulcer, such as a condition in which, in addition to a part of the dermis, a part of subcutaneous tissue (subcutaneous adipose tissue) is deficient or damaged; a condition in which, in addition to a part of the dermis and a part of subcutaneous tissue, a part of the muscle is deficient or damaged; a condition in which, in addition to a part of the dermis, a part of subcutaneous tissue and a part of the muscle, a part of the bone is deficient or damaged; and the skin ulcers with such conditions with a pocket. The skin ulcer with a pocket usually requires surgery to incise and open the pocket before healing. However, by applying the therapeutic material for a skin ulcer according to the present invention, the skin ulcer with a pocket can be effectively treated (reduced/closed) without such surgery.

The decubitus ulcer above can be classified based on the degree of progression of decubitus. For example, when the decubitus is classified based on the degree of progression of decubitus according to the US National Pressure Ulcer Advisory Panel (NPUAP) staging system revised on 2007, a decubitus ulcer in a state in which a part of the dermis is deficient or damaged is classified as decubitus of stage II; a decubitus ulcer in a state in which, in addition to a part of the dermis, a part of subcutaneous tissue is deficient or damaged is classified as decubitus of stage III; and a decubitus ulcer in a state in which, in addition to a part of the dermis and a part of subcutaneous tissue, a part of the muscle and/or bone is deficient or damaged is classified as decubitus of stage IV. The therapeutic material for a skin ulcer according to the present invention has excellent therapeutic effects, which could not be achieved by conventional therapeutic methods, particularly on decubitus classified as stage III to IV.

The fibrous material of the present invention is not particularly limited as long as it can hold an antibiotic and a cell proliferation accelerator therein and is a filamentous material which is stretchable or elastic. Examples of the fibrous material include natural fibers such as silk, wool, cotton, cupra, kapok, flax, hemp, jute, ramie, kenaf, abaca cloth and palm; synthetic fibers such as nylon, polypropylene, polyethylene, polyamide, polyester, polyacrylic and polyurethane; and mixed fibers thereof, preferably cotton among these.

The antibiotic of the present invention is not particularly limited as long as it can inhibit the proliferation or function of microorganism or living cells. Specifically, examples of the antibiotic include sulfadiazine, gentamycin, fradiomycin, colistin, chloramphenicol, kanamycin, polymyxin, Chlomy-P, erythromycin, oxytetracycline, bacitracin, fusidic acid and pharmacologically acceptable salts thereof. Examples of the pharmacologically acceptable salt include acid addition salts such as hydrochloride, hydrobromide, hydroiodide, phosphate, nitrate, sulfate, acetate, propionate, toluenesulfonate, succinate, oxalate, lactate, tartrate, glycolate, methanesulfonate, butyrate, valerate, citrate, fumarate, maleate and malate; metal salts such as sodium salt, potassium salt, calcium salt and silver salt; and ammonium salts and alkylammonium salts. The antibiotic of the present invention is preferably fradiomycin sulfate.

The cell proliferation accelerator of the present invention is not particularly limited as long as it accelerates (activate) cell proliferation directly or it accelerates (activate) cell proliferation by activating signaling pathways that accelerate cell proliferation. In order to treat the decubitus ulcer more effectively, the cell proliferation accelerator preferably has an angiogenesis promoting action and/or a granulation promoting action. Specifically, examples of the cell proliferation accelerator of the present invention include aluminum chlorohydroxy allantoinate, lysozyme chloride, tretinoin tocoferil, bucladesine sodium (Actosin), deproteinized calf blood extract (Solcoseryl), Alprostadil Alfadex, sugar and povidone-iodine and trafermin, preferably trafermin among these.

For the cell proliferation accelerator according to the present invention, the antibiotic and cell proliferation accelerator may be held in liquid moisture (wet) state in the fibrous material. In order to enhance the absorption efficiency and sustained effect of the drugs when contacting the inner surface of a decubitus ulcer, either one or both of the antibiotic and cell proliferation accelerator are preferably held in semisolid state in the presence of a hydrophobic (oleaginous) base (ointment), emulsion base (cream), water soluble base (water soluble ointment), suspension base (gel, jelly, gel) and the like in the fibrous material.

Examples of the hydrophobic (oleaginous) base include hydrocarbons (such as hydrocarbons having 12 to 32 carbon atoms, liquid paraffin, white petrolatum, squalene, squalane and Plastibase), higher alcohols (monohydric aliphatic alcohol having 12 to 30 carbon atoms such as lauryl alcohol, cetyl alcohol, stearyl alcohol or oleyl alcohol), higher fatty acids (saturated or unsaturated fatty acids having 6 to 32 carbon atoms such as palmitic acid or stearic acid), higher fatty acid esters (fatty acid esters such as palmitate myristyl or stearate stearyl; esters of a fatty acid having 10 to 32 carbon atoms and a monohydric aliphatic alcohol having 14 to 32 carbon atoms such as lanolin or carnauba wax; esters of a saturated or unsaturated fatty acid having 10 to 22 carbon atoms and glycerin such as glyceryl monolaurylate or hydrogenated products thereof), vegetable oil and animal oil.

Examples of the emulsion base include an oil-in-water base and a water-in-oil base. Examples of the oil-in-water base include bases formed by emulsifying or dispersing an ingredient such as aforementioned Lanolin, propylene glycol, stearyl alcohol, petrolatum, silicone oil, liquid paraffin, glyceryl monostearate and polyethylene glycol in water phase in the presence or absence of a surfactant. Example of the water-in-oil bases include bases formed by adding water to an ingredient such as petrolatum, higher aliphatic alcohol and liquid paraffin in the presence of a nonionic surfactant to emulsify or disperse it therein.

Examples of the water soluble base include glycols (such as ethylene glycol, propylene glycol and polyethylene glycol).

Examples of the suspension base include an aqueous base in a gel form formed by adding to water starch, glycerin and a suspending agent such as high viscosity carboxymethyl cellulose, carboxyvinyl polymer.

As used herein, "approximately spherical shape" not only refers to a generally spherical shape and a dumpling shape (agglomerated shape like a dumpling) such as ellipsoidal shape, but also refers to an approximately spherical shape having fine irregularities (such as wrinkles, protrusions, depressions) on its surface and/or having voids such as pores and cracks on its surface or in its interior.

The diameter of the approximately spherical shape into which the therapeutic material for a skin ulcer according to the present invention is formed is preferably a diameter enough that the therapeutic material can contact a part of the inner surface of the skin ulcer (preferably 50% or more of the entire inner surface) or substantially the whole of the inner surface (preferably more than 90%) when the fibrous material holding an antibiotic and a cell proliferation accelerator therein is formed into an approximately spherical shape. The diameter may be approximately the same as the inner diameter of the skin ulcer, but considering the fact that the fibrous material is stretchable and elastic, the diameter is preferably somewhat larger than the inner diameter of the skin ulcer in order to enhance the adhesion when the therapeutic material contacts the inner surface of the skin ulcer.

As the therapeutic material for a skin ulcer according to the present invention is characterized in that an antibiotic and a cell proliferation accelerator are contacted with the inner surface of the skin ulcer by forming the therapeutic material into an approximately spherical shape, it is usually applied by placing it on the inner surface of the skin ulcer (preferably on the inner surface of the ulcer at the position as deep as possible, more preferably on the inner surface of the ulcer at the deepest position) so that its majority contacts the inner surface of the skin ulcer, or by packing (pushing) it in the ulcer. Therefore, the application mode is different from the sheet-shaped patch to be used by patching (sticking) it. If necessary, a plurality of the therapeutic materials of the present invention which have been filled with an antibiotic and a cell proliferation accelerator may be contacted with or closely attached to the inner surface of the skin ulcer.

The present invention will be now described in detail by examples to which the present invention is not to be limited.

EXAMPLE

Example 1

1. Confirmation of that the Therapeutic Material of the Invention can Used to Treat Decubitus Ulcers.
1-1 Procedure for Treating Decubitus Ulcers Using the Therapeutic Material of the Present Invention
[1] The wounded surface of a decubitus ulcer, and the interior portion of the tissue site that had been damaged by the decubitus ulcer (a decubitus ulcer classified as stage II according to the NPUAP Staging System [open ulcer], a decubitus ulcer with a pocket of stage III, and a decubitus ulcer of stage IV [huge ulcer]) were thoroughly washed with water or physiological saline.
[2] Depending on the size of the ulcer, one or more sheets of Sofratulle patch 10 cm (manufactured by Sanofi) were made into a dumpling (ball) shape or folded instead of using for its intended use as a patch.
[3] The cotton gauze of Sofratulle patch which was made into a dumpling (ball) shape or folded was sprayed with Fiblast Spray 500 (manufactured by Kaken Pharmaceutical Co., Ltd.) until a trafermin solution was sufficiently penetrated into the gauze, and it was packed deeply in the ulcer.
[4] After confirming that the cotton gauze of Sofratulle patch was in contact with the whole surface of the ulcer, Fiblast Spray 500 was evenly sprayed throughout and the whole ulcer was covered with sterile gauze.
[5] One day later, the cotton gauze of Sofratulle patch packed in the ulcer was removed.
[6] The steps [1] to [5] were repeated.
1-2 Results
1-2-1 Case 1
Patients:
Woman, 88 years old.
Primary disease:
Depression and a right femoral supracondylar fracture. Right knee fixed with a splint for the treatment of such bone fracture. Contracture of the right knee joint. She was diagnosed as decubitus, based on redness caused by the load on contracture region.
Course of treatment:
[1] (2012 Nov. 9) She was diagnosed as a right femoral supracondylar fracture. She had redness in the right knee, was in a drowsy state, and was in the care level 5 group requiring total care.
[2] (2012 Dec. 19) She was diagnosed as decubitus of stage III, and received conventional treatment, i.e., was treated for the ulcer site with Gentamicin [GM] ointment (manufactured by MSD company) and for redness site with Sofratulle patch (manufactured by Sanofi) or Duo Active (manufactured by ConvaTec Inc.).
[3] (2012 Dec. 21) She was diagnosed as decubitus of stage IV. The treatment at the ulcer site ([GM] ointment) was changed to the treatment by both [GM] ointment (manufactured by MSD company) and CADEX ointment (manufactured by Smith & Nephew Wound Management).
[4] (2012 Dec. 26) The bone was exposed and an ulcer with a pocket with 2.0 cm in depth and 5.0 cm×5.0 cm in inner diameter was found. The necrotic tissue was excised (debridement procedure [abbreviated as "debris procedure"]).
[5] (2013 Jan. 11) A large amount of the exudate was discharged. Treatment with both GM ointment and CADEX ointment was continued, but no improvement in the degree of progression of the ulcer was found.
[6] (2013 Feb. 8) Treatment of the decubitus ulcer was started according to the procedure described in "1-1 Procedure for treating decubitus ulcers using the therapeutic material of the present invention".
[7] (2013 Feb. 13) No exudate was discharged but only bleeding was found.
[8] (2013 Mar. 8) The degree of progression of decubitus recovered to stage II.
[9] (2013 Mar. 22) The decubitus ulcer disappeared and the decubitus healed (nearly recovered after six weeks from the start of treatment using the therapeutic material of the present invention).

1-2-2 Case 2
Patients:
Woman, 84 years old.
Primary disease:
Chronic arterial occlusion, schizophrenia, hepatitis B, and decubitus.
Course of treatment:
[1] (2013 Feb. 23) She was diagnosed as decubitus of stage IV. There were found at the sacral region a huge ulcer with 5.0 cm in size and 4.0 cm×4.0 cm in inner diameter and at the base of ulcer a pocket with 5.0 cm in depth.
[2] (2013 Feb. 24) Treatment of the decubitus ulcer was started according to the procedure described in "1-1 Procedure for treating decubitus ulcers using the therapeutic material of the present invention".
[3] (2013 Mar. 5) She had the bone exposed and suffered from strong pain in decubitus site, but the size of the ulcer was reduced to 2.4 cm in depth and 3.2 cm×2.5 cm in inner diameter (see the upper left picture [1] in FIG. 1).
[4] (2013 Apr. 29) The pain disappeared and the size of the ulcer was further reduced to 2.0 cm in depth and 1.5 cm×1.0 cm in inner diameter (see the upper right picture [2] in FIG. 1). The pocket was improved to 3.5 cm in depth.
[5] (2013 May 22) The size of the ulcer was further reduced to 1.8 cm in depth and 1.1 cm×1.0 cm in inner diameter (see the lower left picture [3] in FIG. 1). The pocket was improved to 2.0 cm in depth.
[6] (2013 Nov. 6) The decubitus ulcer was closed and the decubitus healed (see the lower right picture [4] in FIG. 1).

1-2-3 Case 3
Patients:
Man, 89 years old.
Primary disease:
Alzheimer-type dementia, dysphagia, diabetes and decubitus. Conventional treatment with bromelain-GM ointment mixture, Derma Aid treatment with U-PASTA KOWA ointment and Derma Aid treatment was carried out. Nevertheless, he had a poor general condition and was diagnosed as decubitus of stage IV. A plurality of ulcers of various sizes were found in such regions as the elbow region, the sacral region, the greater trochanter region and the knee region.
Course of treatment:
[1] (2014 Jun. 4) A huge ulcer with 6.0 cm in depth and 10.0 cm×8.0 cm in inner diameter was found in the right greater trochanter region (See the left picture in the upper section in FIG. 2). Necroses were found in the edge and periphery of the huge ulcer. Without the debris treatment, decubitus ulcer treatment was started for all the ulcers according to the procedure described in "1-1 Procedure for treating decubitus ulcers using the therapeutic material of the present invention".
[2] (2014 Sep. 3) The huge ulcer was improved to 1.8 cm in depth and 3.0 cm×2.0 cm in inner diameter (See the right picture in the upper section in FIG. 2). Although edema-like granulations were observed in proportion to deterioration of general condition, the necroses in the periphery healed with scar formation. The decubitus ulcers themselves were significantly ameliorated, but the general condition during the treatment showed a deteriorating trend entirely and the patient died 7 hours 40 minutes after taking the picture.

1-3 Discussion
It was difficult to treat and ameliorate intractable decubitus of stage III to IV with the known therapeutic drugs and therapeutic methods (see the course of treatment in Case 1). However, it was demonstrated that treating with the therapeutic material of the present invention could effectively reduce decubitus ulcers and treat decubitus (see the courses of treatment in Cases 1 to 3).

For Fiblast Spray 500, trafermin as its active ingredient is known to have a therapeutic effect on decubitus and skin ulcers, by specifically binding to fibroblast growth factor (FGF) receptors present in cells such as vascular endothelial cells and fibroblasts and thus promoting angiogenesis and granulation (see "Tanaka E, et al., Biol. Pharm. Bull., 19, 1141-1148 (1996)"). Sofratulle patch is a loose cotton gauze which has fradiomycin sulfate as its active ingredient and the purified lanolin and white petrolatum as its additive substance evenly adhered and permeated thereto. In consideration of these features, the present inventor has considered a mechanism for treating intractable decubitus with the dumpling-shaped Sofratulle patch into which a trafermin solution is penetrated. He has expected that 1) by forming Sofratulle patch into a dumpling shape, fradiomycin sulfate (antibiotic) as its active ingredient was effectively adhered and permeated throughout the base of ulcers or the interior portion of the ulcers with a pocket to effectively inhibit bacterial infections at the base of ulcers or in the ulcers with a pocket, and thus, 2) the angiogenesis and granulation promoting action of trafermin (angiogenesis and/or granulation promoting agent) was maximized to result in reducing decubitus ulcers and healing intractable decubitus.

All patients of the above-mentioned three cases experienced no adverse effect of treatment. Although two patients (Cases 1 and 2) among them were cases of intractable decubitus, in Case 1, decubitus healed 6 weeks after starting treatment, and in Case 2, a pain arising from decubitus disappeared two months after starting treatment and thereafter decubitus healed. Although one patient (Case 3) died of deterioration of general condition, decubitus continued to be ameliorated and the result was marked amelioration until the day of death.

Based on the above results, it has been believed that treatment of decubitus ulcers with the therapeutic material of the present invention is an effective treatment which results in an immediate effect, causes a pain associated with reduction of ulcer size to disappear and generates an extremely high satisfaction degree of a patient.

INDUSTRIAL APPLICABILITY

The therapeutic material for a skin ulcer of the present invention is effective for the treatment of critical skin ulcers such as intractable decubitus with pockets and huge intractable decubitus ulcers, and for the treatment of severe decubitus that have progressed to stage III to IV according to the NPUAP Staging System, particularly decubitus with intractable ulcers with pockets or decubitus with huge intractable ulcers, for which no sufficient therapeutic methods have been established.

The invention claimed is:
1. A method for treating a decubitus skin ulcer, comprising packing a piece of cotton holding an antibiotic and a cell proliferation accelerator into a decubitus skin ulcer with a pocket and classified as stage III-IV when the degree of progression of decubitus is classified according to the US National Pressure Ulcer Advisory Panel (NPUAP) staging system revised in 2007, whereby the cotton is formed so as to contact the whole of the inner surface of the skin ulcer.
2. The method according to claim 1, wherein the cell proliferation accelerator has angiogenesis and/or granulation promoting actions.
3. The method according to claim 1, wherein the cell proliferation accelerator is trafermin.

4. The method according to claim 1, wherein the antibiotic is fradiomycin sulfate.

5. The method according to claim 1, wherein the skin ulcer is a decubitus skin ulcer classified as stage IV when the degree of progression of decubitus is classified according to the US National Pressure Ulcer Advisory Panel (NPUAP) staging system revised in 2007.

6. The method according to claim 2, wherein the cell proliferation accelerator is trafermin.

7. The method according to claim 2, wherein the antibiotic is fradiomycin sulfate.

8. The method according to claim 3, wherein the antibiotic is fradiomycin sulfate.

9. The method according to claim 6, wherein the antibiotic is fradiomycin sulfate.

10. The method according to claim 1, wherein the skin ulcer is a decubitus skin ulcer.

11. The method according to claim 2, wherein the decubitus skin ulcer is intractable.

* * * * *